United States Patent
Höglund (10) Patent No.: US 9,730,699 B2
(45) Date of Patent: Aug. 15, 2017

(54) DEVICE AND METHOD FOR TISSUE LIGATION

(71) Applicant: Resorbable Devices AB, Uppsala (SE)

(72) Inventor: Odd Höglund, Uppsala (SE)

(73) Assignee: RESORBABLE DEVICES AB, Uppsala (SE)

( * ) Notice: Subject to any disclaimer, the term of this patent is extended or adjusted under 35 U.S.C. 154(b) by 201 days.

(21) Appl. No.: 14/413,032

(22) PCT Filed: May 22, 2013

(86) PCT No.: PCT/SE2013/050582
§ 371 (c)(1),
(2) Date: Jan. 6, 2015

(87) PCT Pub. No.: WO2014/007719
PCT Pub. Date: Jan. 9, 2014

(65) Prior Publication Data
US 2015/0157327 A1    Jun. 11, 2015

(30) Foreign Application Priority Data

Jul. 6, 2012    (SE) .................................... 1250787

(51) Int. Cl.
*A61B 17/08*    (2006.01)
*A61B 17/12*    (2006.01)
*A61B 17/00*    (2006.01)

(52) U.S. Cl.
CPC .................. *A61B 17/12009* (2013.01); *A61B 2017/00004* (2013.01)

(58) Field of Classification Search
CPC . A61B 17/12009; A61B 17/12; A61B 17/122; A61B 17/82; A61B 17/08; A61B 17/1322; A61F 2/08
See application file for complete search history.

(56) References Cited

U.S. PATENT DOCUMENTS

| 3,463,427 | A | * | 8/1969 | Fisher | F16L 3/2332 24/16 PB |
| 4,001,898 | A | * | 1/1977 | Caveney | F16L 3/2332 24/16 PB |
| 7,127,779 | B2 | | 10/2006 | Hewes | |
| 8,696,692 | B2 | * | 4/2014 | Hoglund | A61B 17/12009 606/151 |
| 2005/0288674 | A1 | | 12/2005 | Golobek | |

FOREIGN PATENT DOCUMENTS

| WO | 2009/021104 A2 | 2/2009 |
| WO | 2009/091313 A1 | 7/2009 |

* cited by examiner

*Primary Examiner* — Victor Nguyen
(74) *Attorney, Agent, or Firm* — Porter Wright Morris & Arthur LLP (57) ABSTRACT

A medical device for tissue ligation contains a band having perforations and rungs. A locking case is connected to the band and has a channel dimensioned for reception of the band. A locking member of the locking case is configured to interlock perforations and rungs in the band. The channel contains an arching portion into which the band at least partly protrudes by arching over the locking member when the locking member engages a rung of the band.

11 Claims, 8 Drawing Sheets

DEVICE AND METHOD FOR TISSUE LIGATION

TECHNICAL FIELD

The present embodiments generally relate to medical devices, and in particular to such medical devices for tissue ligation.

BACKGROUND

Ligation is the medical act of restricting blood flow in a blood vessel or other tissue. Traditionally, tissue ligation is conducted using a ligature usually in the form of a suture thread or string, tied around the tissue. Other prior art ligation devices include metal or polymer clips that are pinched around the tissue.

Even though the ligature is a very simple device, the act of tissue ligation can be cumbersome, sometimes requiring the operation of more than one medical person. For instance, in some surgical operations the tissue to become ligated needs to be lifted slightly from surrounding tissue in a subject. However, tying the ligature thread around the lifted tissue typically requires two hands, in particular when tightening the thread around the tissue and locking the thread with a knot. In these cases, the tissue has to be lifted, potentially by another medical person, from the surroundings or the surrounding tissue has to be withdrawn.

There is therefore a need for a medical device that has the potential of being used for tissue ligation and can be operated with one hand. The design of a cable tie's self-locking loop offers such an opportunity.

US 2005/0288674 discloses a bio-absorbable bone tie having a convex locking case and an elongated band used for securing fragments of a fractured bone together. The bone tie is basically constructed as a traditional cable tie with the exception of the convex locking case.

U.S. Pat. No. 4,001,898 discloses a self-locking cable tie with a head carrying a non-pivotal locking means extending into an aperture through the head and securely engaging a selected abutment of a strap of the cable tie. Pusher means is carried by the head and extends into the aperture. The pusher means is responsive to retrograde movement of the strap to push the abutment to be held into engagement with the locking means.

WO 2009/091313 discloses a medical device comprising an elongated, flexible band equipped with ratchet members and connected to a device head having a channel dimensioned for reception of the band. A lock member is connected to the device head and configured to interlock the ratchet members when the band is pulled through the channel to form a reverse-motion brake. A protrusion and a matching protrusion receiving member are arranged in the device head in connection with the channel entrance and in the band in connection with the band-locking case interface. The protrusion receiving member is dimensioned for reception of the protrusion when the band is close to fully pushed into the device head.

SUMMARY

It is a general objective to provide a medical device suitable for tissue ligation.

It is a particular objective to provide a medical device that provides a reverse-motion brake with a rigid locking member.

These and other objectives are met by embodiments disclosed herein.

An aspect of the embodiments relates to a medical device for tissue ligation. The medical device comprises an elongated, flexible band having a front side, a rear side, a leading end and a trailing end. The band has perforations and rungs defined therein. A locking case is connected to the trailing end of the band and has a channel dimensioned for reception of the band. A locking member is connected to the locking case and is disposed in connection with the channel. The locking member is configured to interlock perforations and rungs defined in the band. The locking channel in the locking case comprises an arching portion arranged opposite to the locking member. The band is configured to arch over the locking member and protrude at least partly into the arching portion when the locking member engages a rung of the band.

Another aspect of the embodiments relates to a tissue ligation method. A leading end of a band of a medical device as defined above is inserted into a channel of a locking case of the medical device to form a loop around a tissue to be ligated. The leading end of the band is pulled through the channel to lock the band around the tissue, constrict blood vessel(s) in the tissue and thereby achieve a tissue ligation.

The medical device of the embodiments can be used in connection with rigid locking members that are needed when using soft materials for medical device and where the locking member does not have sufficient spring-like locking capability

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Throughout the drawings, the same reference numbers are used for similar or corresponding elements.

The present embodiments relate to a medical device suitable for ligation of tissues and vessels in an animal body, such as a mammalian body, including a human body, and to a method of using such a medical device in performing tissue ligation.

The medical device, ligature, of the embodiments has significant advantages over the prior art thread-based ligatures. Firstly, the medical device can be handled by one hand of a medical person, leaving the other hand free for lifting the tissue to be ligated slightly out from the surrounding body. Furthermore, the locking of the medical device is simplified and does not require tying any knots in the limited space where the surgical operation is taking place in the animal or human body.

The medical device of the present embodiments is based on the principles of a cable tie (also denoted strap, zip tie, mouse belt, tie wrap, tie rap and quick draw in the art) for allowing forward motion of a band relative to a locking member but restricting or even fully preventing backward movement of the band relative to the locking member. This feature of cable tie, providing a reverse-motion brake, replaces the cumbersome operation of tying knots of sutures/ligatures and thereby significantly simplifies the ligation process.

Prior art medical devices for tissue ligation that are based on the principles of a cable tie typically have a flexible locking member attached to a locking case. This flexible locking member then springs or swings up and down as a band of the medical device is pulled through a channel in the locking case. Thus, when the locking member engages a rung in the band it is bent or pushed towards its base in the locking case. However, when the band is moved a bit further into the channel so that the locking member becomes aligned with a perforation or indentation in the band the locking member springs back and protrudes into the perforation or indentation. This springing or swinging up and down of the locking member is continued as long as the band is being pulled through the channel.

Such a design of the medical device requires that the medical device or at least the locking member of the medical device is made of a material that can support the necessary spring-like behavior of the locking member. Hence, such prior art solutions put limitations to the type of materials that can be used for the medical device.

The present embodiments provide a medical device with a locking case and locking member that can be used also for materials that do not possess the spring-like behavior. This means that, for instance, softer polymer material can be used and still enable an efficient locking of the band to the locking case. Hence, a reverse-motion brake is obtained even without any springing or swinging of the locking member as the band is being pulled through the channel in the locking case.

The present embodiments have taken a radically different approach by designing the channel through the locking case to have an arching portion arranged opposite to the locking member. When the band is being pulled through the channel the band alternates between an arched configuration protruding at least partly into the arching portion of the channel when the locking member engages a rung of the band and a flat configuration when the locking member protrudes into a perforation of the band. Hence, it is the band that arches back and forth during the movement through the channel, whereas the locking member remains substantially rigid and still in the locking case.

An aspect of the embodiments relates to a medical device for tissue ligation. The medical device comprises an elongated, flexible band having a front side, a rear side, a leading end and a trailing end. The band further has perforations and rungs defined therein. The medical device also comprises a locking case connected to the trailing end of the band and has a channel dimensioned for reception of the band. A locking member is connected to the locking case and is disposed in connection with the channel. This locking member is configured to interlock perforations and rungs defined in the band. The channel in the locking case comprises an arching portion arranged substantially opposite to the locking member. The band is configured to arch over the locking member and protrude at least partly into the arching portion when the locking member engages a rung of the band.

Various embodiments of this aspect will now be further described in connection with the drawings.

Figure 1:
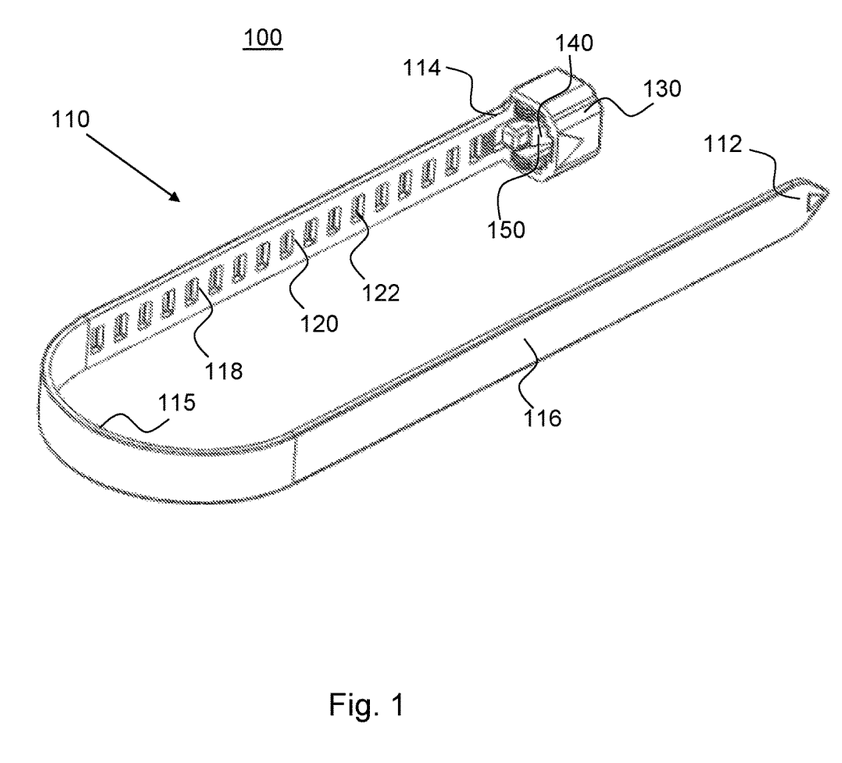
FIG. 1 is an illustration of a medical device according to an embodiment.

FIG. 1 is an illustration of a particular embodiment of a medical device 100 suitable for tissue ligation. The medical device 100 comprises an elongated, flexible band or strip 110 having a front side 118 and an opposite rear side 116. A trailing end 114 of the band 110 is attached and anchored to a locking case or head 130 of the medical device 100. The opposite leading end 112 of the band 110 is adapted for insertion into a channel 150, through-hole or aperture running through the locking case 130.

Figure 9:
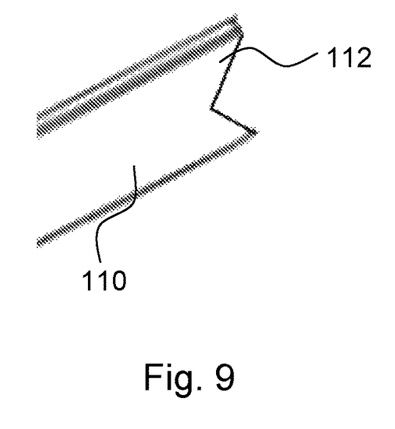
FIG. 9 is a magnification of the leading end of the band according to an embodiment.

The leading end 112 can be pointed for facilitating guiding of the band 110 into the channel 150. The leading end 112 could even be sharp to be able to penetrate tissue, when such a function is required. It is also possible to have a Y-shaped or forked leading end 112, which could facilitate introduction of the leading end 112 into the channel 150 of the locking case 130, see FIG. 9.

The reverse-motion braking action of the medical device 100 is achieved through perforations 122 and rungs 120, also denoted ratchet members in the art, provided in at least a portion of the band 110. The perforations 122 and rungs 120 are preferably arranged on at least the front side 118 of the band 110 but could also, or instead, be present on the rear side 116.

The perforations 122 and rungs 120 are arranged on at least the portion of the band 110 that is closest to the trailing end 114 and the locking case 130. As a consequence, the perforations 122 and rungs 120 can start at the trailing end 114 or close to the trailing end 114 and run at least a distance up through the band length towards the leading end 112. It is actually possible to have perforations 122 and rungs 120 along the whole length of the band 110 but for most practical applications it is sufficient to have the perforations 122 and rungs 120 up to a sub-part of the band lengths. In this context, the important feature is that the perforations 122 and rungs 120 should be provided at least up to a portion of the band length towards the leading end 112 to engage a locking member 140 in the locking case 130 when the leading end 112 is fed into the channel 150 and the band 110 forms a loop around a tissue to be ligated. Thus, the largest diameter of the loop when the locking member 140 first starts engaging with the perforations 122 and rungs 120 as the leading band end 112 is pulled through the channel 150 should preferably be larger than the outer diameter of the tissue present in the loop. For most practical applications, the perforations 122 and rungs 120 could therefore extend over a length of the band 110 that is from about one or few centimeters up to several centimeters.

Figure 5:
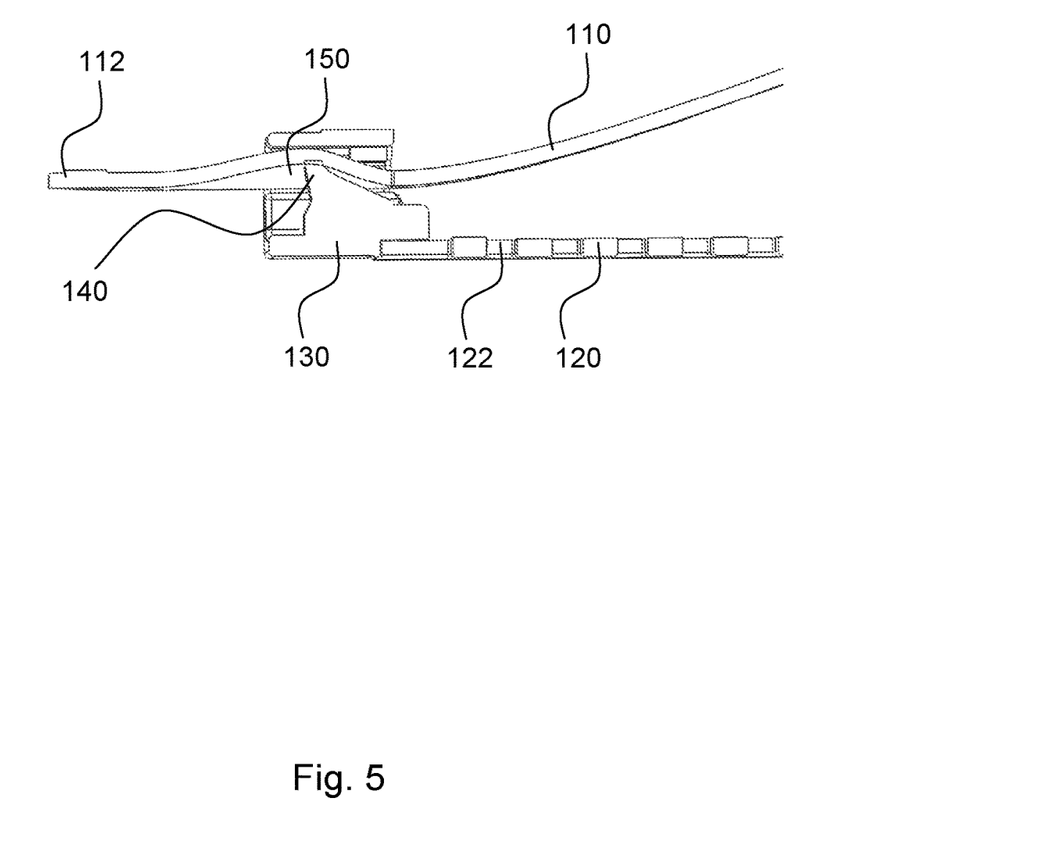
FIG. 5 is cross-sectional view of part of the medical device shown in FIG. 4.

The perforations 122 and rungs 120 can, in a first embodiment, be realized as an array of through-holes or apertures 122 through the band 110 as illustrated in FIG. 1 and more clearly seen in the cross-sectional view of FIG. 5. These holes 122 form, together with the intermediate band material, i.e. rungs 120, a ladder structure that can be engaged by the locking member 140 in the locking case 130 to achieve the reverse-motion brake. In a second embodiment, the perforations 122 and rungs 120 are instead a plurality of notches in the front side 118 or the rear side 116 of the band 110. These notches, thus, form indentations in the band 110 but not necessarily penetrate through the whole thickness of the band 110 as in the first embodiment. The intermediate band material between the notches then corresponds to the rungs 120. A third embodiment is to replace the holes or notches with a plurality of protruding members, such as ratchet teeth forming the rungs 120, extending a short distance from the front or rear side surface.

The locking case 130 comprises the locking member 140 disposed in connection with the channel 150, which is running through the locking case 130 and is dimensioned for reception of the band 110. The locking member 140 could be in the form of at least one lock tooth or latching element dimensioned to interlock perforations 122 and rungs 120 defined in the band 110. In the case of hole- or notch-implemented perforations 122 and rungs 120, the locking member 140 is arranged for step-by-step protrusion into the holes or notches as the band 110 is being fed through the channel 150. Correspondingly, the locking member 140 engages with the protrusion of a ratchet teeth solution as the band 110 is being pulled through the channel 150 in the locking case 130.

The inter-engagement between the locking member 140 and the perforations 122 and rungs 120 permits forward movement of the band 110 through the channel 150 but restrains the band 110 against reverse movement through the channel 150, thereby achieving a reverse-motion brake.

Figure 2:
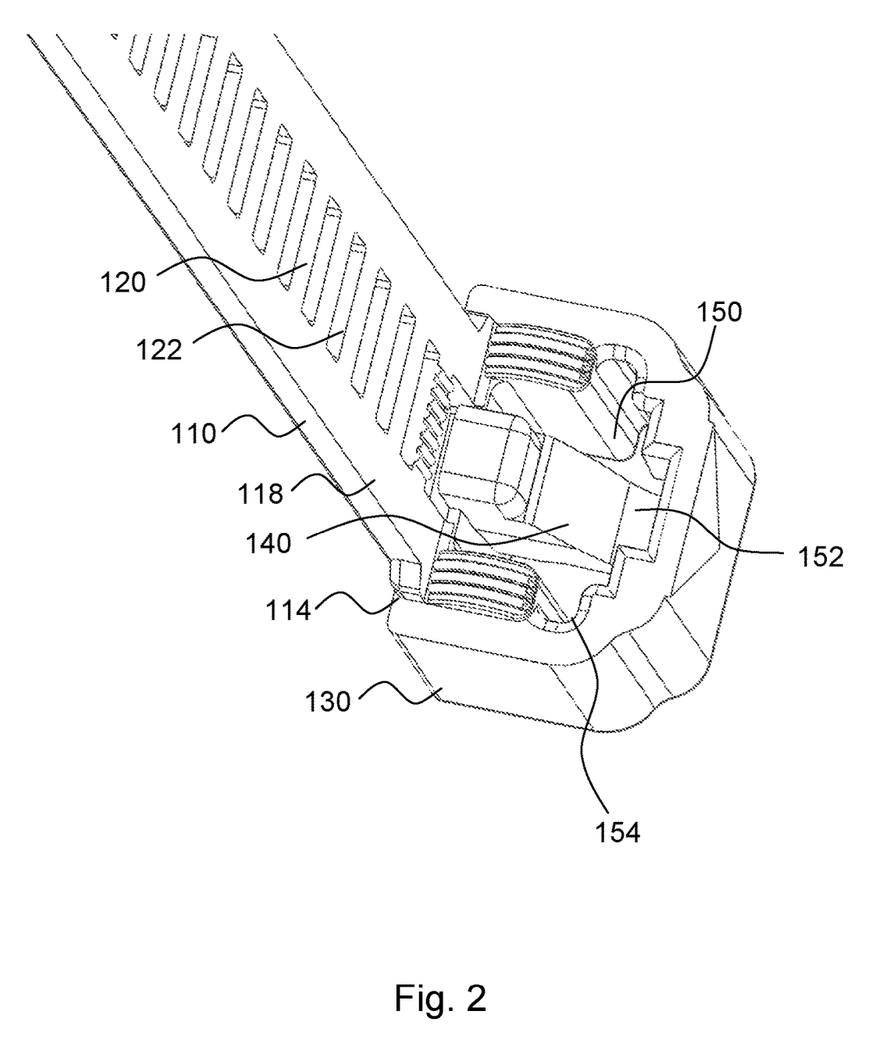
FIG. 2 is a magnification of the locking case in the medical device of FIG. 1 from a first view.
Figure 3:
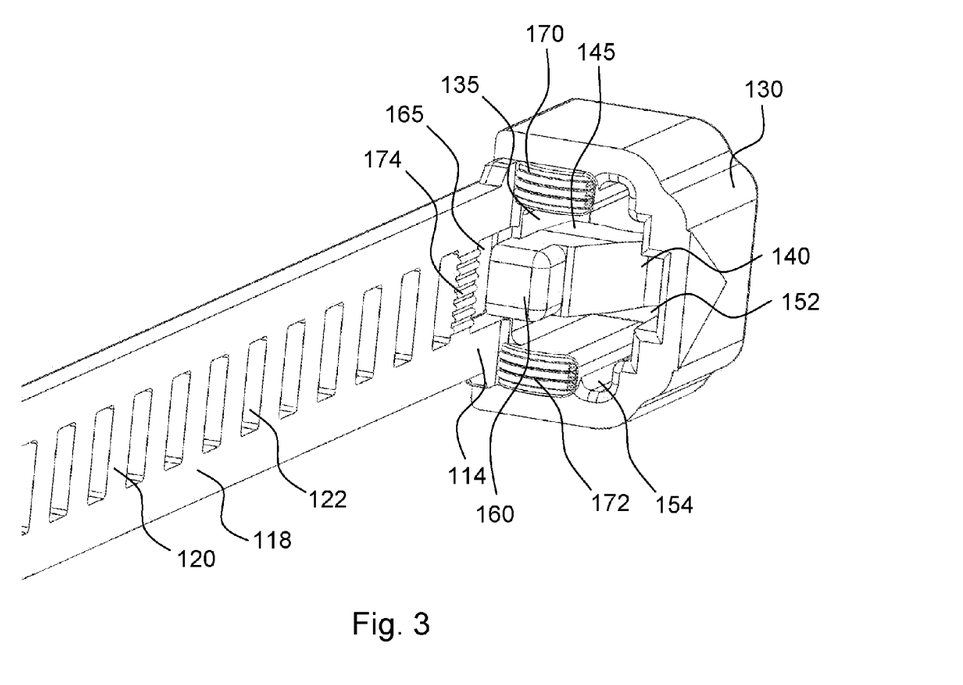
FIG. 3 is a magnification of the locking case in the medical device of FIG. 1 from a second view.

The locking member 140 is more clearly shown in FIGS. 2 and 3. As is seen in these figures, the locking member 140 preferably ramps upward from the entrance side to the exit side of the channel 150, while the opposite face of the locking member 140 drops vertically. It is anticipated by the present embodiments that the lock member 140 may include multiple locking teeth, such as positioned in series or as a train in connection with, preferably in, the channel 150.

The locking member 140 preferably has a base portion that is fully attached to a wall 135 of the channel 150 in the locking case 130. This means that the locking member 140 forms a rigid structure with a solid attachment to the locking case 130. Hence, in a particular embodiment the locking member 140 is substantially inflexible and is preferably configured to maintain a rigid configuration when the band 110 is being pulled through the channel 150.

The locking member 140 is disposed in connection with the channel 150 and is preferably, as is illustrated in FIGS. 1 to 3, provided somewhere along the length of the channel 150. Alternatively or in addition, the locking member 140 could be provided in connection with the entrance and/or exit of the channel 150 in the locking case 130.

The locking member 140 can be situated in connection with the inner wall 135 of the locking case 130 that is on the same side of the channel 150 as the band 110. The perforations 122 and rungs 120 are then provided on at least the front side 118 of the band 110. Alternatively, the locking member 140 is provided on the inner wall opposite to the side of the channel 150 at which the band 110 is anchored to the locking case 130. The perforations 122 and rungs 120 are then provided on at least the rear side 116 of the band 110.

Figure 4:
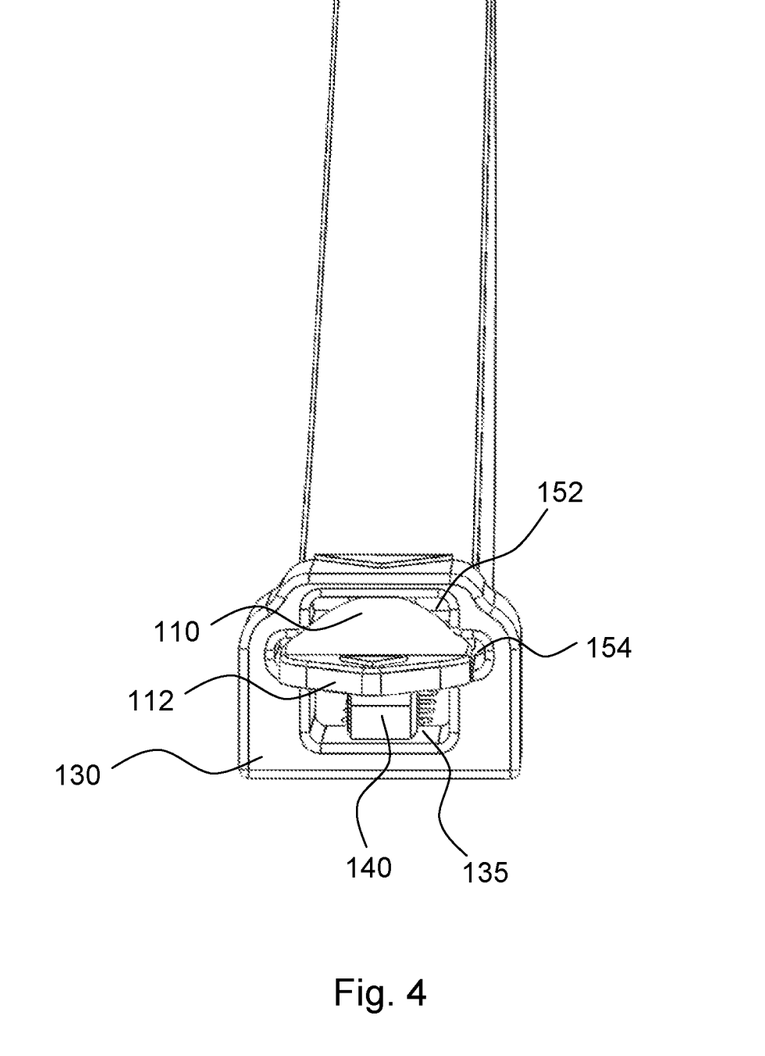
FIG. 4 illustrates a view of the medical device with the band pulled partly through the channel of the locking case.

According to the embodiments, the channel 150 comprises, as is more clearly shown in FIGS. 2 and 3, an arcing portion 152 that constitutes the portion of the channel 150 that is substantially opposite to the locking member 140. This arching portion 152 enables the band 110 to arch over the locking member 140 when the locking member 140 is aligned with and engages a rung 120 in the band 110. This is shown in FIGS. 4 and 5 where a portion of the band 110 protrudes or extends at least partly into the arching portion 152.

Hence, when the locking member 140 engages a rung 120 in the band 110 the locking member 140 pushes at least a central part (with regard to a transversal dimension or extension of the band 110 opposite to the longer longitudinal dimension) of the band 110 into the arching portion 152 of the channel 150. Thus, according to a particular embodiment the locking member 140 is preferably rigid enough not to spring or swing back when engaging a rung 120 in the band 110 but in clear contrast pushes on the band 110 to force the portion of the band 110 aligned with the locking member 140 to protrude at least partly into the arching portion. FIG. 5 is a cross-sectional view of the locking case 130 and a portion of the band 110 showing how the locking member 140 pushes the band 110 into the arching portion 152 of the channel 150.

When the band 110 is pulled a bit further through the channel 150 so that the locking member 140 now becomes aligned with a perforation 122, the locking member 140 will protrude at least partly into the perforation 122. At this point the locking member 140 does no longer push against the band 110. Hence, the band 110 will move or spring back into a basal portion 154 of the channel 150 and thereby no longer protrude into the arching portion 152. This basal portion 154 is shown in FIGS. 3 and 4 and preferably comprises the portion of the channel 150 that faces the locking member 140.

When the band 110 is being pulled through the channel 150 the band 110 preferably alternates between extending substantially in the basal portion 154 when the locking member 140 is aligned with and protrudes into a perforation 122 of the band 110 and protruding at least partly into the arching portion 152 when the locking member 140 is aligned with and engages a rung 120 of the band 110.

When the band 110 is extending substantially in the basal portion 154, a portion of the band 110 present in the channel 150 has basically a flat cross-sectional configuration with regard to a cross-section along the transversal dimension of the band 110. The cross-sectional configuration will, hence, typically correspond to a rectangular (assuming that the thickness of the band 110 is smaller than the width of the band 110). However, when the band 110 protrudes at least partly into the arching portion 152, the portion of the band 110 present in the channel 150 typically has an arched cross-sectional configuration. The cross-sectional configuration will, hence typically correspond to an arch or arc.

As clearly shown in FIGS. 2-4 and 6, the basal portion 154 and the arching portion 152 preferably have different extensions along the width of the locking case 130. In particular, the basal portion 154 preferably has a wider extension as compared to the arching portion 152. This means that the basal portion 154 could be viewed as a slot through the locking case 130 and with the arching portion 152 present at a central (with regard to the extension along the width of the locking case 130) part of the basal portion 154. The extension of the basal portion 154 preferably corresponds to or is slightly wider than the width of the band 110, whereas the extension or width of the basal portion 152 is preferably narrower than the width of the band 110. Hence, when the band 110 is moved through the channel 150 and the locking member 140 is aligned with and engages a rung 120 of the band 110, the central (with regard to the width of the band 110) part of the band 110 is pushed into the arching portion 152. The peripheral (with regard to the width of the band 110) parts of the band 110 are, however, preferably still present in the basal portion 154 since there is not room for the complete band 110 to be moved from the basal portion 154 to the arching portion 152. When the locking member 140 is aligned with and protrudes into a next perforation 122 of the band 110 the central part of the band 110 is moved back towards the basal portion 154 so that the complete part of the band 110 present in the channel 150 is preferably in the basal portion 154.

In a preferred embodiment, the band 110 automatically engages the locking member 140 when the locking member 140 is aligned with a perforation 122 in the band 100. Thus, when given the chance the band 110 will leave the arched configuration, which is a stressed and energy-dependent position, and level out once the band 110 is moved from a position with the locking member 140 aligned with a rung 120 to the locking member 140 aligned with a perforation 122 in the band 110.

In an optional embodiment, the medical device 100 comprises at least one tissue engaging member 170, 172 arranged on a side of the locking case 130 comprising the channel entrance and into which the leading end 112 of the band 110 is inserted. The tissue engaging member 170, 172 is more clearly seen in FIGS. 3 and 6. The tissue engaging member 170, 172 preferably comprises multiple studs, ridges or hooks for engaging the tissue as the band 110 is being pulled through the channel 150 to restrict any relative motion and slipping between the tissue and the medical device 100. The tissue gripping or engaging action of the tissue engaging member 170, 172 reduces the risk that the medical device 100 would slide off the tissue during and after ligation, which is a common problem today with (extensive) bleeding as a result. Such ligature sliding according to the prior art during and/or after operation lengthens the operation time and/or requires a new surgical procedure to attach a new ligature around the tissue. Thus, preventing or at least restricting any tissue sliding during and after ligation is an advantageous feature of the medical device 100 of the present embodiment.

Figure 8:
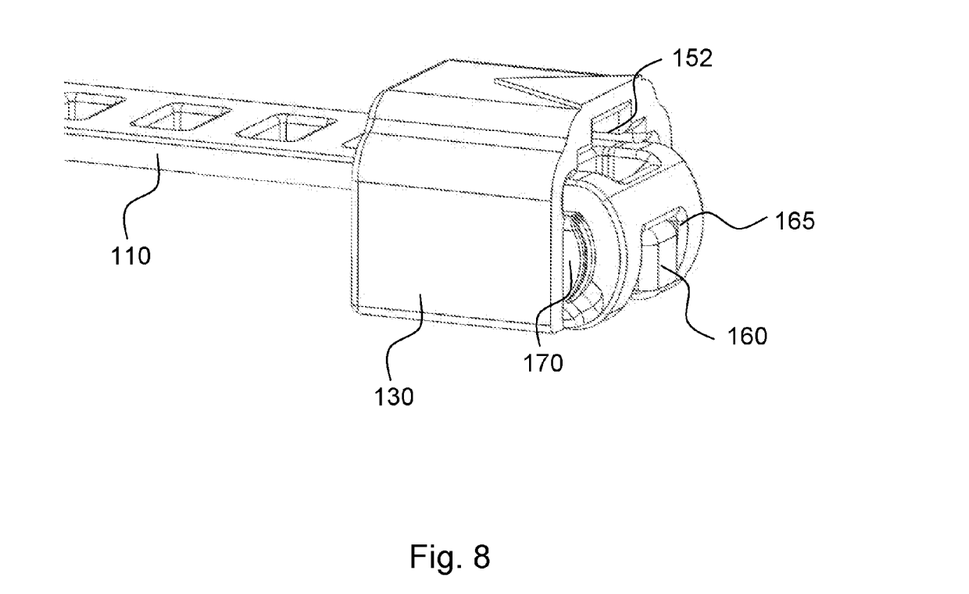
FIG. 8 is a magnification of the locking case with the band fully pulled through the channel of the locking case.

In a preferred embodiment, the tissue engaging member 170, 172 comprises a first tissue engaging member 170 and a second tissue engaging member 172 arranged on opposite sides of the channel 150 on the side of the locking case 130 containing the channel entrance. More preferably, the two tissue engaging members 170, 172 are positioned on the locking case 130 to protrude against the front side 118 of the band 110, when the band 110 is fed through the channel 150, as is seen in FIG. 8. This means that the tissue engaging members 170, 172 also help reducing the band loop diameter to small values, such as zero or even negative diameter. FIG. 8 clearly illustrates how the trailing end 114 of the band 110 aligns around tissue engaging member 170 at this band-feeding stage.

Another advantage of the tissue engaging member(s) 170, 172 is that it squeezes or crushes blood vessels in the tissue during ligation, thereby preventing or at least reducing any bleeding.

In alternative embodiments, the tissue engaging member 170, 172 is not necessarily arranged in the locking case 130. In clear contrast, the tissue engaging member is then provided on the band 110, preferably in connection with the trailing end 114. In such a case, the tissue engaging member is typically present on the front side 118 of the band 110 for pressing, when the band 110 is being pulled into the channel 150, the tissue to ligate against the locking case 130. Correspondingly, in the case of multiple tissue engaging members one or all of these can be present on the band 110. Thus, these embodiments also encompass an embodiment having at least one tissue engaging member in the locking case 130 and at least one tissue engaging member on the band 110.

Figure 6:
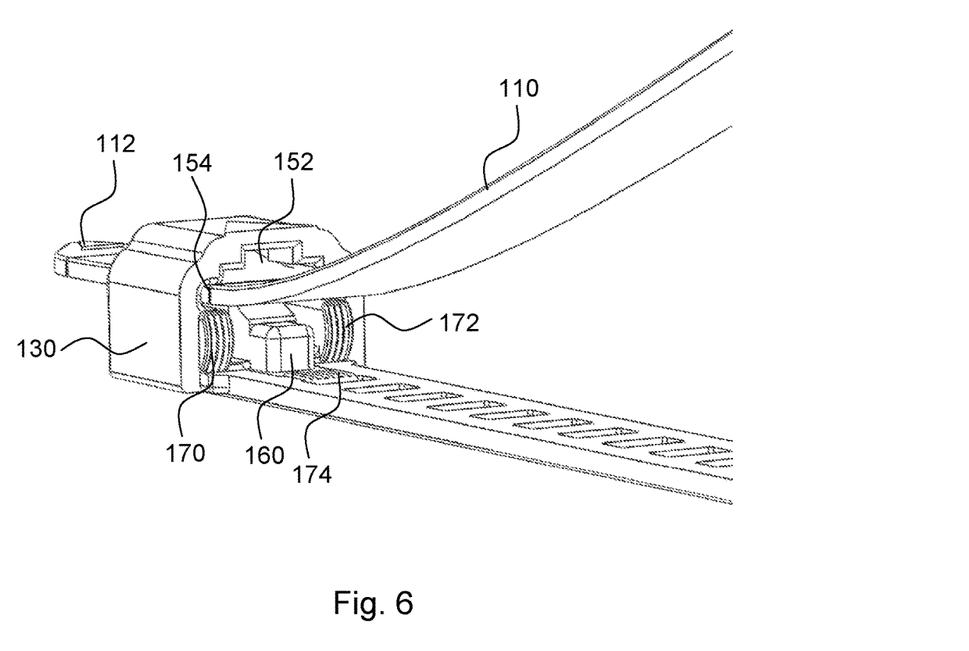
FIG. 6 illustrates another view of the medical device with the band pulled partly through the channel of the locking case.

In other optional embodiments, the medical device 100 comprises another, or an additional, tissue engaging member 174 as shown in FIGS. 3 and 6. This tissue engaging member 174 is preferably arranged on the front side 118 of the band 110 in connection with the trailing portion 114 of the band 110. The tissue engaging member 174 is in the form of protrusions extending beyond the general surface of the front side 118. The protrusions may be in the form of ridges as shown in the figure but could alternatively be circular elevations, studs, hooks, or any other tissue engaging structure.

The tissue engaging member 174 can cover substantially the major portion of the front side 118 that is closest to the locking case 130 possibly excluding portions of the front side 118 occupied by the perforations 122 and rungs 120. In the embodiment illustrated in FIG. 3, the tissue engaging member 174 is substantially present on the lowest rung of the band 110. In an alternative approach, the tissue engaging member 174 is only present on a portion of a rung. A further implementation is to have the tissue engaging member 174 present not only on a rung but further extending towards the sides of the band 110. Thus, in this approach the tissue engaging member 174 extends substantially all over the transversal dimension of the band 110 or at least over a major portion thereof.

It is anticipated by the embodiments that in most applications with rung-implemented tissue engaging member 174, it is generally enough to have the tissue engaging member 174 arranged on the lowest rung as is illustrated in the figure. However, it is indeed possible to have the tissue engaging member 174 also provided on rungs more distance from the locking case 130.

The tissue engaging member 174 arranged on the front side 118 of the band 110 has similar tissue engaging effects as the above-described tissue engaging members 170, 172 provided in the locking case 130. In other words the tissue engaging member 174 reduces the risk that the medical device 100 would slide of the tissue during and after the ligation.

The medical device 100 can be equipped with the band-arranged tissue engaging member 174 as the sole tissue engaging structure. Alternatively, this tissue engaging member 174 is complemented with the one or both tissue engaging members 170, 172 arranged in the locking case 130 as illustrated in the figure. A further embodiment is to only use the head-implemented tissue engaging member(s) 170, 172. Still another embodiment of the medical device 100 does not have any dedicated tissue engaging members.

Figure 7:
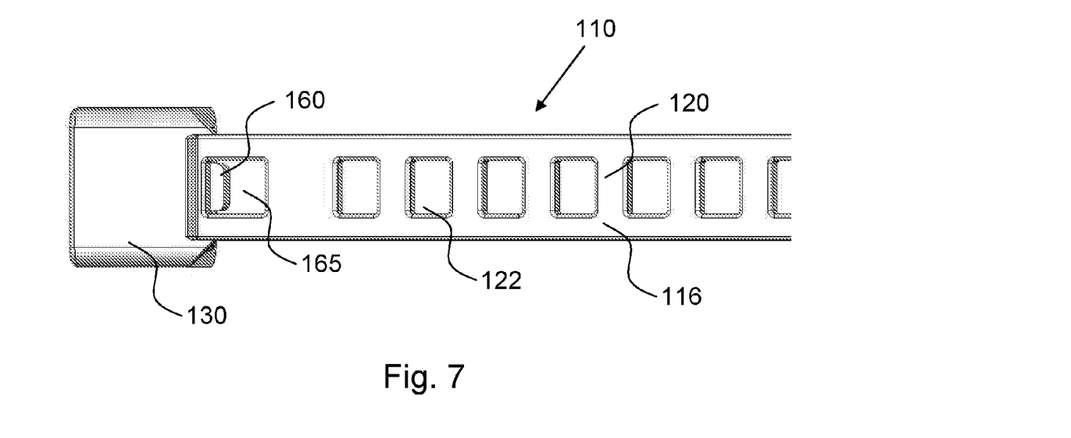
FIG. 7 is a magnification of the back side of the locking case and the trailing portion of the band.

In an optional embodiment, the medical device 100 may comprise a protrusion 160 arranged, in this embodiment, in the locking case 130 in connection with the entrance to the channel 150, see FIGS. 3, 6 and 7. A matching protrusion receiving member 165 is provided in the band 110 in connection with the trailing end 114. The protrusion receiving member 165 is dimensioned for allowing reception of the protrusion 160.

The protrusion 160 is preferably arranged on the same side of the channel 150 in the locking case 130 as the trailing end 114 is connected to the locking case 130. Correspondingly, the protrusion receiving member 165 is preferably arranged in the portion of the band 110 that is in the interface or next to the transition between the band 110 and the locking case 130.

In an alternative embodiment, the respective positions of the protrusion 160 and the protrusion receiving member 165 are interchanged, i.e. the protrusion 160 is provided in the band 110 with the protrusion receiving member 165 on the locking case 130.

When the leading end 112 of the band 110 is fed through the channel 150 and is almost fully pulled through the channel 150 to reduce the dimension of the band loop, the protrusion 160 in the locking case 130 enters the protrusion receiving member 165 in the band 110. Since the protrusion 160 enters the protrusion receiving member 165, the band 110 can be further pulled through the channel 150 to even further reduce the band loop diameter. It is actually possible, through the inclusion of the protrusion 160 and the protrusion receiving member 165, to reduce the loop diameter to zero and even less than zero or negative. FIG. 8 illustrates the locking case 130 with the band 110 inserted into the channel 150 and fully pulled through the channel 150. As is seen in the figure, no loop is present between the band 110 and the locking case 130 at this position as the protrusion 160 enters the protrusion receiving member 165.

This reduction and minimization of loop diameter allows the usage of the medical device 100 even when ligating very thin tissue samples, such as small blood vessels. The protrusion 160 and its matching protrusion receiving member 165 allow the band 110 to be fully fed through the channel 150 with no loop diameter left outside of the entrance to the channel 150.

The protrusion receiving member 165 can be realized as an aperture or indentation 165 defined, in an embodiment, in the band 110, where the aperture or indentation 165 has a dimension, i.e. inner circumference, and depth in the case of indentation, which matches the dimension, i.e. outer circumference and height, of the protrusion 160 to allow the protrusion 160 to enter the aperture or indentation 165 when the band 110 is fully or almost fully fed through the channel 150. In the case of an indentation embodiment, the indentation is preferably provided in the front side 118 of the band 110 as illustrated in the figure. The aperture 165 with its matching protrusion is also seen in FIG. 7, which illustrates a backside view of a portion of the medical device 100.

The medical device 100 of the above described optional embodiments basically achieves a double ligation, thereby significantly increasing the chances of successful tissue ligation. Thus, a first ligation operation occurs between a first stringer or stile of the band 110 and the protrusion 160 in combination with the tissue engaging member 170. A second ligation operation is correspondingly achieved between a second stringer or stile of the band 110 and the protrusion 160 in combination with the tissue engaging member 172. In practical applications using prior art ligatures, two ligatures are often positioned next to each other on the tissue to ligate for security reasons. Embodiments disclosed herein relax this need for usage of multiple separate ligatures as the medical device 100 itself can provide two ligations separated a few millimeters from each other, depending on the width of the protrusion 160.

In order to simplify handling of the medical device 100 and in particular simplify entering the leading band end 112 into the channel 150 in the locking case 130 using a single hand, an intermediate portion 115 of the band 110 between the leading end 112 and the trailing end 114 is optionally bent, see FIG. 1. A preferred embodiment has a U-shaped intermediate portion 115 to position the leading end 112 close to the locking case 130 even when the band 110 has not yet been introduced into the channel 150.

Due to the U-shape of the intermediate band portion 115, a medical person positions the ligating tissue in the space formed between the two, almost parallel, band portions between the trailing end 114 and the intermediate portion 115 and the leading end 112 and the intermediate portion 115. At this position, the medical person can, using one hand, introduce the leading band end 112 into the channel 150 and pull the band 110 therethrough to start the tissue ligation.

In a typical embodiment, the medical device 100 is manufactured as a single piece, for instance by molding the medical device 100 in a suitable polymer material. In an alternative embodiment, the locking case 130 and the locking member 140 are manufactured, such as molded, as a single piece and with the band 110 as another single piece. These two pieces can then be attached together, for instance by gluing or fused together in another way. In a further embodiment, a two-component injection molding machine or equipment could be used to manufacture the medical device 100. In such a case, a first polymer material can be used for the solid band 110 and a second, different polymer material is used for the locking case 130, the locking member 140 and the perforated part of the band 110. In this approach, polymer materials with different properties can be used for the different pieces. For instance, a non-resorbable, cheaper polymer material could be used for the solid band 110, whereas a resorbable, typically more expensive polymer material could be used for the locking case 130, the locking member 140 and the perforated part of the band 110.

The material of the medical device 100 is a biocompatible material, which does not have any major toxic or injurious effects on the animal or human body. Examples of such biocompatible materials include hypoallergenic materials traditionally employed for implantable medical devices. Currently preferred materials include biocompatible polymer materials and in particular resorbable or bio-absorbable polymers.

Examples of such resorbable polymers that can be used according to the embodiments include polyglycolide, poly-L-lactide, poly-p-dioxanone, poly(trimethylene carbonate), polycaprolactone and copolymers derived from two or more monomers selected from glycolide, L-lactide, p-dioxanone, trimethylene carbonate and ε-caprolactone.

However, also other monomers could be used to form resorbable polymers or copolymers, for instance, δ-valerolactone, β-butyrolactone, ε-decalactone, 2,5-diketomopholine, pivalolactone, α-diethylpropiolactone, ethylene carbonate, ethylene oxalate, 3-methyl-1,4-dioxane-2,5-dione, 3,3-diethyl-1,4-dioxan-2,4-dione, γ-butyrolactone, 1,4-dioxepan-2-one, 1,5-dioxepan-2-one, 1,4-dioxan-2-one, 6,8-dioxabicycloctane-7-one, and combinations thereof. Further suitable resorbable materials that can be used according to the present invention are described in U.S. Pat. Nos. 4,968,317 and 4,898,186, the teachings of which regarding resorbable, biocompatible materials is hereby incorporated by reference.

Resorbable materials imply that the medical device 100 can be left in the animal or human body and are resorbed by the body following a time after the surgical procedure. Thus, an advantage of using a resorbable medical device 100 is that the tissue response is restricted and limited in extent and time and no further surgical procedure is required for removing the medical device 100 after the ligation operation has been completed and the ligated tissue has healed. This saves both costs and suffering from the relevant human or animal patient. The use of resorbable materials significantly reduces or removes the risk of chronic tissue reactions, thereby reducing the risk that the implant needs to be prematurely removed.

The design of the medical device 100 and in particular of the channel 150 with its arching portion 152 and rigid locking member 140 is in particular suitable for usage with resorbable polymer materials. A reason for this is that such resorbable polymer materials may be softer as compared to non-resorbable polymer materials. This means that using a traditional approach with a locking member springing and swinging up and down as the band is being pulled through the channel of the locking case might not be possible due to the softness and thereby lack of springing effect of the resorbable polymer material. This means that the design of the medical device 100 according to the embodiments enables usage of polymer materials that are not suitable or even possible to use in connection with prior art designs of cable ties.

Although the medical device 100 is preferably made of a polymer material also non-polymeric or non-plastic materials, such as metal materials or metal alloy materials, such as titanium, titanium alloys and stainless steel, can be used as long as the band material is flexible enough to allow being bent when pulling the leading end 112 of the band 110 through the channel 150 in the locking case 130 and to allow arching over the locking member 140 to protrude at least partly into the arching portion 152 of the channel 150.

The actual size of the medical device 100 is not decisive for the teachings of the present embodiments and can be selected based on the particular application, animal/human subject and/or tissue to be ligated.

However, in most typical implementations, the length of the band 110 could be from about one or few centimeters to one or more decimeters, with a thickness from the range of sub-millimeters to one or more millimeters and a width from the range of sub-millimeters to one or more millimeters. The width and/or thickness of the band 110 must not necessarily be uniform. In clear contrast, the leading end 112 could be narrower and/or thinner than the trailing end 114 to thereby facilitate insertion of the leading end 112 into the channel 150. Correspondingly, the length of the band portion from the leading end 112 up to the intermediate portion 115 could be somewhat longer than the band portion from the trailing end 114 up to the intermediate portion 115. This prevents the leading end 112 from easily dropping out of the locking case 130 once introduced into the channel 135.

Figure 10:
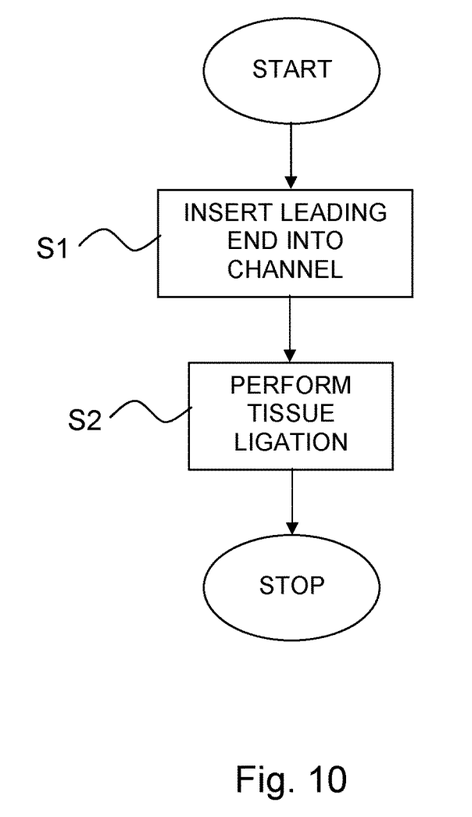
FIG. 10 is a flow diagram of a tissue ligation method according to an embodiment.

FIG. 10 is a flow diagram illustrating the use of the medical device 100 of the embodiments in a tissue ligation method. The method starts in step S1, where a leading end 112 of the band 110 of the medical device 100 is inserted into the channel 150 of the locking case 130 to form a band loop enclosing a tissue to be ligated. Finally, the leading end 112 is pulled through the channel 150 to snare the tissue and achieve a ligation. The design of the medical device 100 allows the leading end 112 to be pulled using a single hand operation, thereby leaving the other hand free to remove surrounding tissue that must not be ligated. Due to the inter-engagement of the perforations 122 and rungs 120 and the locking member 140, the band 110 is prevented from reverse movement and opening of the ligation loop. As the band 110 is being pulled through the channel 150 the band 110 alternates between a flat cross-sectional configuration extending in the basal portion 154 of the channel 150 and an arched cross-sectional configuration protruding at least partly into the arched portion 152 of the channel 150.

It is anticipated that any surplus band portion extending beyond the channel exit in the locking case 130 after fully pulling the band 110 tight around the tissue can be cut off by the medical person.

The medical device 100 can be used for ligating vastly varying tissues in both human and animal, preferably mammalian animal bodies. Non-limiting examples include ligation of blood vessels, such as veins and arteries, for instance during laparoscopy; fallopian tube ligation/tubal ligation; uterine horn; uterine body or testicular funicle, for instance during ovariohysterectomy and castration; during spleen ectomy or intestinal, pulmonary or cardiac procedures. The medical device 100 can also be used in any soft tissues surgery, in or outside the abdominal or thoracic cavity, where a ligation is desired. The medical device 100 can therefore be utilized instead of traditional ligatures but also replace devices such as stapling equipment, ultrasonic scalpels, vessel sealing devices, transfixation ligatures, surgeons knot and other knots, e.g. Miller's knot.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A medical device for tissue ligation comprising:
an elongated, flexible band having a front side, a rear side, a leading end and a trailing end, and having perforations and rungs defined therein;
a locking case connected to said trailing end of said band and having a channel dimensioned for reception of said band; and
a locking member connected to said locking case and disposed in connection with said channel and configured to interlock perforations and rungs defined in said band, wherein
said channel in said locking case comprises an arching portion arranged opposite to said locking member; and
said band is configured to arch over said locking member and protrude at least partly into said arching portion when said locking member engages a rung of said band.

2. The medical device according to claim 1, wherein
said channel comprises a basal portion facing said locking member; and
said band is configured to extend in said basal portion when said locking member protrudes into a perforation of said band.

3. The medical device according to claim 2, wherein said band is configured to alternate, when said band is being pulled through said channel, between i) extending substantially in said basal portion, in which a portion of said band present in said channel has a flat cross-sectional configuration, when said locking member protrudes into a perforation of said band, and ii) protruding at least partly into said arching portion, in which said portion of said band present in said channel has an arched cross-sectional configuration, when said locking member engages a rung of said band.

4. The medical device according to claim 2, wherein said basal portion has an extension along a width of said locking case that is at least larger than a width of said band and said arching portion has a shorter extension along said width of said locking case than said extension of said basal portion and said width of said band.

5. The medical device according to claim 1, wherein said locking member is rigidly arranged on a wall of said channel in said locking case.

6. The medical device according to claim 1, wherein said locking member is substantially inflexible and is configured to maintain a rigid configuration when said band is being pulled through said channel.

7. The medical device according to claim 1, wherein said medical device is at least partly made of a resorbable polymer.

8. The medical device according to claim 1, wherein said medical device is at least partly made of a polymer selected from a group consisting of polyglycolide, poly-L-lactide, poly-p-dioxanone, poly(trimethylene carbonate), polycaprolactone and copolymers derived from two or more monomers selected from a group consisting of glycolide, L-lactide, p-dioxanone, trimethylene carbonate and $\epsilon$-caprolactone.

9. The medical device according to claim 1, wherein said medical device is molded as a single piece.

10. The medical device according to claim 1, wherein said locking case and said locking member are molded as a single piece and said single piece is attached to said band.

11. A tissue ligation method comprising:
inserting a leading end of a band of a medical device according to claim 1 into a channel of a locking case of said medical device to form a loop around a tissue; and
pulling said leading end of said band through said channel to lock said band around said tissue and achieve a tissue ligation.

* * * * *